(12) United States Patent
Maier et al.

(10) Patent No.: US 12,193,967 B2
(45) Date of Patent: Jan. 14, 2025

(54) APPLICATOR FOR A PESSARY DEVICE

(71) Applicant: Reia, LLC, Lyme, NH (US)

(72) Inventors: Kaitlin Maier, Darien, CT (US);
Meegan Daigler, Portland, ME (US);
Ariana Sopher, Portland, ME (US);
Katie Lim, Brooklyn, NY (US)

(73) Assignee: Reia, LLC, Lyme, NH (US)

( * ) Notice: Subject to any disclaimer, the term of this patent is extended or adjusted under 35 U.S.C. 154(b) by 379 days.

(21) Appl. No.: 17/690,735

(22) Filed: Mar. 9, 2022

(65) Prior Publication Data
US 2022/0296411 A1    Sep. 22, 2022

Related U.S. Application Data

(60) Provisional application No. 63/164,382, filed on Mar. 22, 2021.

(51) Int. Cl.
*A61F 6/12* (2006.01)
*A61F 2/00* (2006.01)

(52) U.S. Cl.
CPC .............. *A61F 6/12* (2013.01); *A61F 2/0022* (2013.01); *A61F 2/005* (2013.01)

(58) Field of Classification Search
CPC ...... A61F 6/00; A61F 6/12; A61F 6/06; A61F 6/08; A61F 6/18; A61F 13/266; A61F 13/26; A61F 13/32; A61F 2/0022; A61F 2/005
USPC ...................................... 604/15; 128/834–841
See application file for complete search history.

(56) References Cited

U.S. PATENT DOCUMENTS

| | | | |
|---|---|---|---|
| 4,361,150 A | * | 11/1982 | Voss ..................... A61M 31/007 604/59 |
| 8,062,245 B2 | | 11/2011 | Gann et al. |
| 8,127,768 B2 | | 3/2012 | Ziv |
| 8,449,491 B2 | | 5/2013 | Hasse et al. |
| 8,449,492 B2 | | 5/2013 | Sargent, Jr. et al. |
| 10,383,777 B2 | | 8/2019 | De Soto-Burt et al. |
| 10,617,503 B2 | | 4/2020 | Rosen et al. |
| 2002/0111578 A1 | * | 8/2002 | Buzot ..................... A61F 13/26 604/14 |
| 2006/0111661 A1 | | 5/2006 | Gann et al. |
| 2006/0155240 A1 | | 7/2006 | Osborn, II et al. |
| 2006/0161096 A1 | | 7/2006 | Osborn, II et al. |
| 2015/0060317 A1 | | 3/2015 | De Soto-Burt et al. |
| 2019/0231587 A1 | * | 8/2019 | Spitz .......................... A61F 6/12 |
| 2019/0282350 A1 | | 9/2019 | Conti |
| 2020/0306077 A1 | | 10/2020 | Sopher et al. |

FOREIGN PATENT DOCUMENTS

WO    WO-2021015625 A1 *    1/2021    ............. A61F 6/144

* cited by examiner

*Primary Examiner* — Caitlin A Carreiro
(74) *Attorney, Agent, or Firm* — Hinckley, Allen & Snyder, LLP; David R. Josephs

(57) ABSTRACT

An applicator for inserting a pessary, the applicator including a barrel and a plunger. The barrel having an upper chalice shaped opening having a first diameter at the top most edge and a second diameter at an intermediate location lower than the top most edge. The first diameter is larger than the second diameter. The plunger is configured to at least partially receive a pessary and is telescopically received in the barrel. The plunger is configured and arranged to eject the pessary from the barrel upon telescopic movement of the plunger within the barrel towards the top most edge.

19 Claims, 17 Drawing Sheets

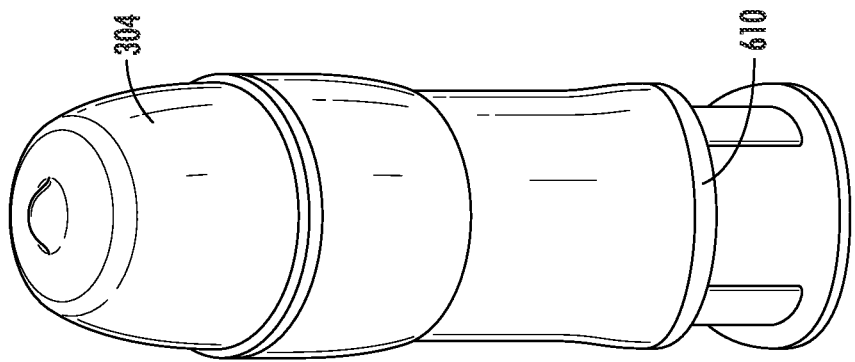
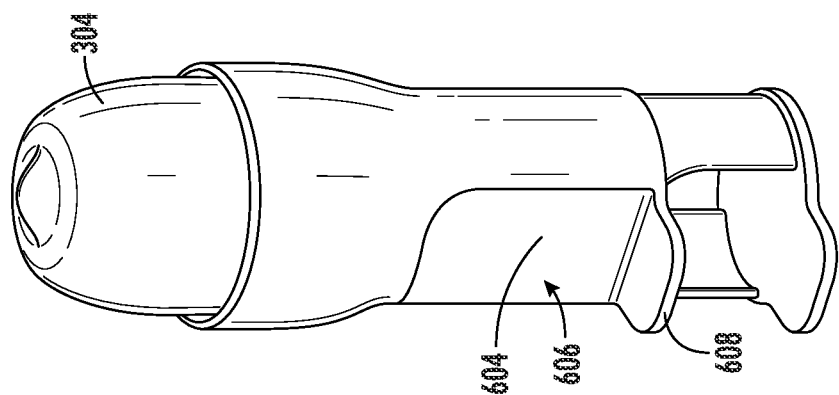
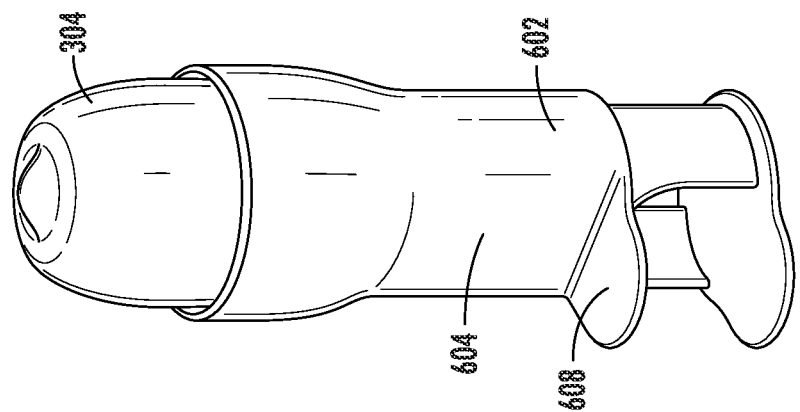

APPLICATOR FOR A PESSARY DEVICE

CROSS REFERENCE TO RELATED APPLICATION

This application claims priority from earlier filed U.S. Provisional Application No. 63/164,382, filed on Mar. 22, 2021, the entire contents of the foregoing being incorporated herein by reference.

GOVERNMENT LICENSE RIGHTS

This disclosure was made with government support under a Phase I Small Business Innovation Research grant awarded by the National Institute of Health, grant application ID: 1 R43 HD097809-01 and a Phase II Small Business Innovation Research grant awarded by the National Institute of Health, grant application IDs: 2 R44 HD097809-02 and 5 R R44 HD097809-03. The government has certain rights in the disclosure.

BACKGROUND OF THE INVENTION

This disclosure relates to pessaries for use in treating pelvic organ prolapse (POP). More specifically, the present disclosure provides applicators for use in placing pessaries for use in treating pelvic organ prolapse.

About 50 percent of women over the age of 50 suffer from some degree of pelvic organ prolapse. The female pelvic organs include the bladder, uterus, vagina, and rectum. A prolapse is a medical condition in which at least one organ of the body has collapsed forward, backward, or downward. Pelvic organ prolapse can result from weakening of the pelvic floor muscles and loss of integrity of the pelvic floor connective tissue, which allows for abnormal uterine or vaginal descent. In certain cases, the uterus or portions of the vagina can descend through the opening to the vagina. Symptoms of pelvic organ prolapse include pelvic discomfort, difficulty with urinating and voiding, and sexual dysfunction.

Contributory factors for pelvic organ prolapse can include a history of pregnancy and childbirth, advanced age, smoking, obesity, connective tissue disorders upper respiratory disorders, repetitive strain injuries, and neuropathies. The severity of pelvic organ prolapse can range from minor and asymptomatic to more severe degrees requiring medical intervention. In the latter case, women can choose to undergo reconstructive surgery using a surgically implanted mesh or a native tissue repair to resuspend the fallen structures. As an alternative to surgery, women can manage their prolapse with a pessary. In this regard, the present disclosure is directed to applicators for insertion and positioning of such pessary devices to provide non-surgical management of pelvic organ prolapse.

The prior art depicted at FIG. 1 presents a case of pelvic organ prolapse in which certain of the pelvic organs have descended from a female pelvic region 100. The female pelvic region 100 is shown in a side view such that the front side 102 is oriented to the left and the rear side 104 is to the right. The pelvic region 100 is supported by a skeletal frame 106. A plurality of prolapsed organs 108 have descended from the pelvic region below the pelvic floor axis 109 that corresponds to a plane running from front to rear along the bottom of the pelvic region. Ordinarily, the pelvic organs are disposed above axis 109. The prolapsed organs 108 that have descended below axis 109 include a bladder 110, a uterus 112, and the vagina 114. In the case of the vagina 114, this organ has become inverted, such that the interior lining is now an exterior surface, to the great discomfort of the person for whom it is an ordinary recessed organ. A rectum 116 remains situated above axis 109, but it is contemplated that eventually, it can descend through axis 109 to join the other prolapsed organs 108.

As known in the art, a pessary is a device that can be inserted into the vagina to support the descending organs. Pessaries can be recommended for women who do not wish to undergo surgery, for pregnant women, or for women with other serious health issues which makes surgery too risky. Pessaries are primarily made of medical grade silicone, with some containing internal support structures for added rigidity. Some pessaries are made entirely or partially of acrylic. In function, the pessary is positioned in the vaginal canal to provide support for the descending organs.

For example, the prior art pessary device of FIG. 2A, as shown inserted in FIG. 3, is an attempt to manage and treat pelvic organ prolapse, commonly known as a "Gellhorn" pessary. This prior art pessary 200 is inserted into the vagina 114 to support the prolapsed organs 108 depicted at FIG. 1. The pessary 200 can be placed in the vagina 114 just above axis 109 and can stay in place due to residual tone of the pelvic floor muscle group 202 or as a function of at least one of suction, a frictional force and/or larger size (so as to cause the vaginal wall to indent around the perimeter of the pessary 200). When in position, the pessary supports the organs above it, and it prevents them from impinging upon or passing through the vaginal introitus (opening).

However, pessaries can cause erosion of the vaginal lining (epithelium) if they are inappropriately sized or left in situ for prolonged periods. To fit a pessary, a healthcare practitioner (for example, a physician, a physician's assistant, a nurse, or midwife) assesses the size of the vaginal introitus 204 and depth. The pessary can be lubricated, inserted, and positioned behind the pubic symphysis 206 (a bony structure in the skeletal frame 106). Pessaries in the prior art tend to be rigid and difficult to remove and re-insert by the user alone. Many women return to the practitioner every three to six months to have their pessary removed, cleaned, and replaced. Some women are able to remove and clean their pessaries themselves. The recommendations for self-cleaning have not been standardized, but for example, current pessary product inserts advise any woman who is able to remove her own pessary to remove, wash and replace it daily. Pessaries can be cumbersome and uncomfortable to insert and remove. The average pessary user is a postmenopausal woman and these women often experience vaginal atrophy and dryness as well as narrowing of the vaginal canal and introitus, creating the potential for further difficulty and discomfort of insertion and removal.

Currently available pessaries are manually folded or compressed to some degree before insertion, if possible. Although this can be helpful with enhancing the ease and comfort of the insertion, currently available pessaries are not able to significantly decrease in cross-sectional area. Further, due to their rigid design, current pessaries are difficult to hold in the manually folded or compressed state, especially for women attempting to insert the pessary themselves. During removal it can be difficult to fold the pessary, often resulting in the pessary being removed in its full or close to full size and shape, which causes discomfort and difficulty. These attributes make self-maintenance of the pessary very painful, if not impossible, and consequently, few women with a pessary are able to remove, clean, and insert their own pessaries. Furthermore, some pessaries are not removable by the patient at all. Therefore, existing pessary devices in the prior art are not easily removed and, therefore, may not address an important need for the non-surgical management and treatment of pelvic organ prolapse.

While the ring with support pessary 201(as shown in FIG. 2B) of the prior art does contain holes (which serve the function of allowing for drainage of fluids), the holes can also be used by patients and physicians as a feature to grab for increased leverage during removal. However, the holes are located within the body of the ring pessary, making them difficult to reach. The Gellhorn pessary 200 prior art device has a protruding stem with a knob; however, the stem is more for alignment once in place than removal (as evidenced by the existence of a "short stemmed" pessary). The knob is relatively small in diameter. The vast majority of patients are unable to grasp it for removal and practitioners need to use forceps to grip the knob for removal. When the pessary is lubricated to attempt to minimize the pain and tearing with insertion, or when it is lubricated after having been in the vagina, this further increases the difficulty of holding the pessary during both insertion and removal.

The relative rigidity of pessaries and the difficulties in removal can result in a reliance on a healthcare practitioner for regular cleaning, an inability to experience vaginal intercourse and the pessary remaining inserted even when not necessary. It would be desirable for an applicator for a pessary to be readily inserted and removed by the user, thereby improving the quality of life for that user.

Moreover, an applicator for a pessary that better enables self-maintenance additionally increases accessibility to prolapse management would be advantageous over prior art devices. In under resourced areas, where access to the frequent medical care needed for prolapse maintenance is difficult, a pessary applicator that enables users to easily insert a pessary themselves can increase the opportunity for treatment. Even when pessaries are handled by a skilled practitioner, the process of insertion can often be painful. Therefore, there is a particular need for a pessary applicator device that can be used to easily insert a pessary by the user without the assistance of a medical practitioner.

SUMMARY OF THE INVENTION

The present disclosure preserves the advantages of the support provided by prior art pessary devices. In addition, it provides new advantages not found in currently available pessaries and overcomes many disadvantages of such currently available pessaries.

The pessary applicator of the present disclosure overcomes the disadvantages of the prior art, by providing a pessary applicator that can allow for easy and unencumbered pessary insertion for self-management of the pessary without the assistance of a health or medical practitioner. The present disclosure provides a novel pessary applicator device that improves the ease of insertion of the pessary for both patients and practitioners. The pessary of the present disclosure generally includes an applicator with a barrel and a plunger that can retain the pessary for application to the patient. The plunger can be depressed after the applicator and pessary are inserted into the patient. When depressed, the plunger ejects the pessary from the barrel, and the pessary is deployed within the patient. In some embodiments, the plunger and the barrel can include a number of combinations of ergonomic features which allow for ease of use.

Due to the typical older demographic of pessary wearers, many suffer from osteoarthritis and limited dexterity. These users are particularly in need of assistance with the insertion of their pessary device when self-managing the device on their own. Thus, the unique ergonomic features of the present disclosure are particularly helpful for these older pessary wearers. Further, the disclosed pessary applicator can additionally, or alternatively, include several additional features that permit ease of disassembly of the plunger and barrel for cleaning purposes.

Therefore, the present disclosure provides a pessary and applicator device that is more easily inserted without pain. Further, the present disclosure provides a pessary applicator device that can be managed by the wearer themselves. Finally, the present disclosure provides a pessary applicator device that does not suffer from the disadvantages in the prior art.

BRIEF DESCRIPTION OF THE DRAWING FIGURES

The novel features which are characteristic of the present disclosure are set forth in the appended claims. However, the preferred embodiments, together with further objects and attendant advantages, will be best understood by reference to the following detailed description taken in connection with the accompanying drawings in which:

Figure 6:
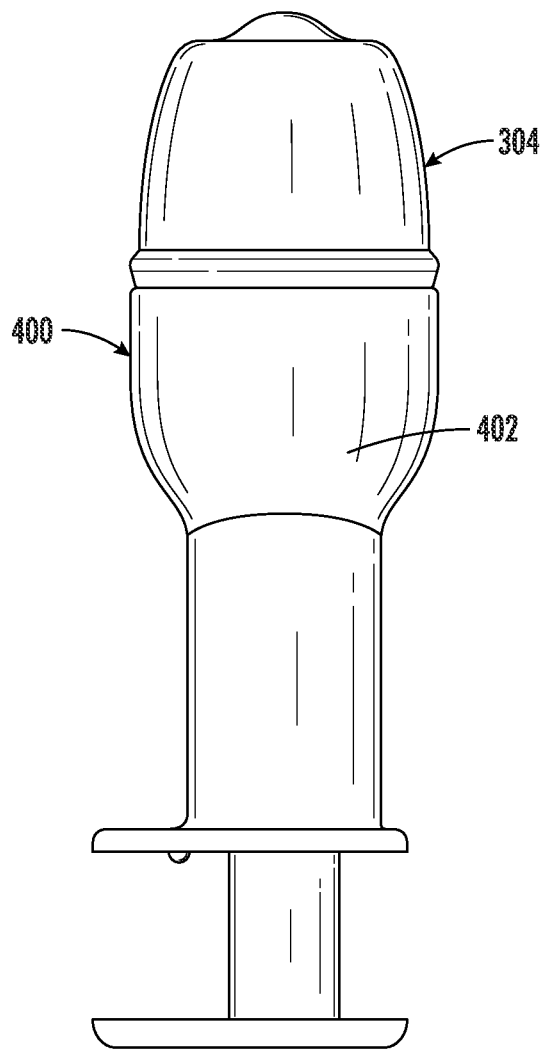
Figure 7:
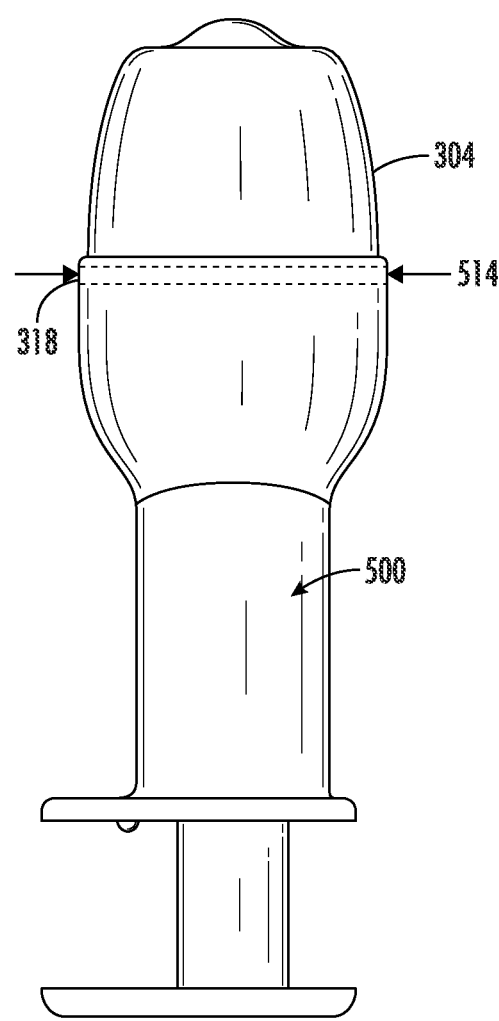
Figure 11:
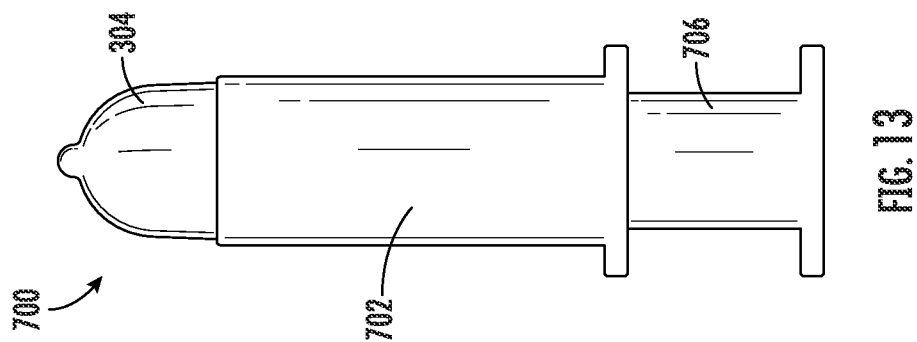
Figure 12:
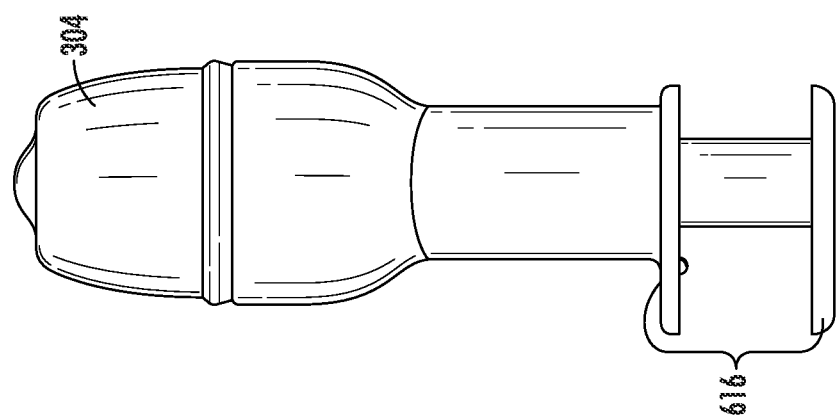
Figure 13:
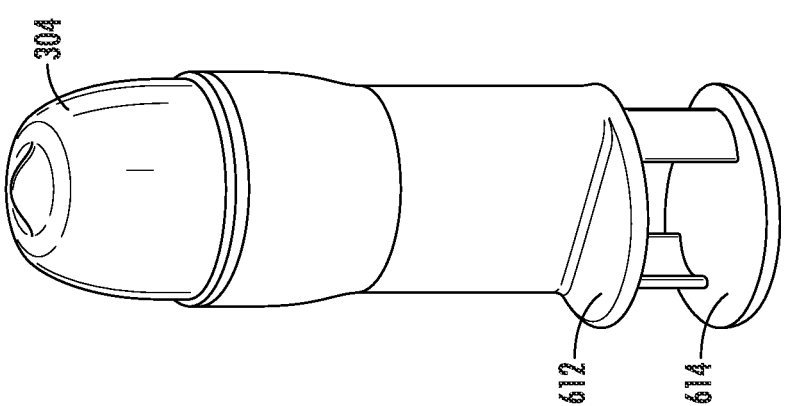
Figure 15B:
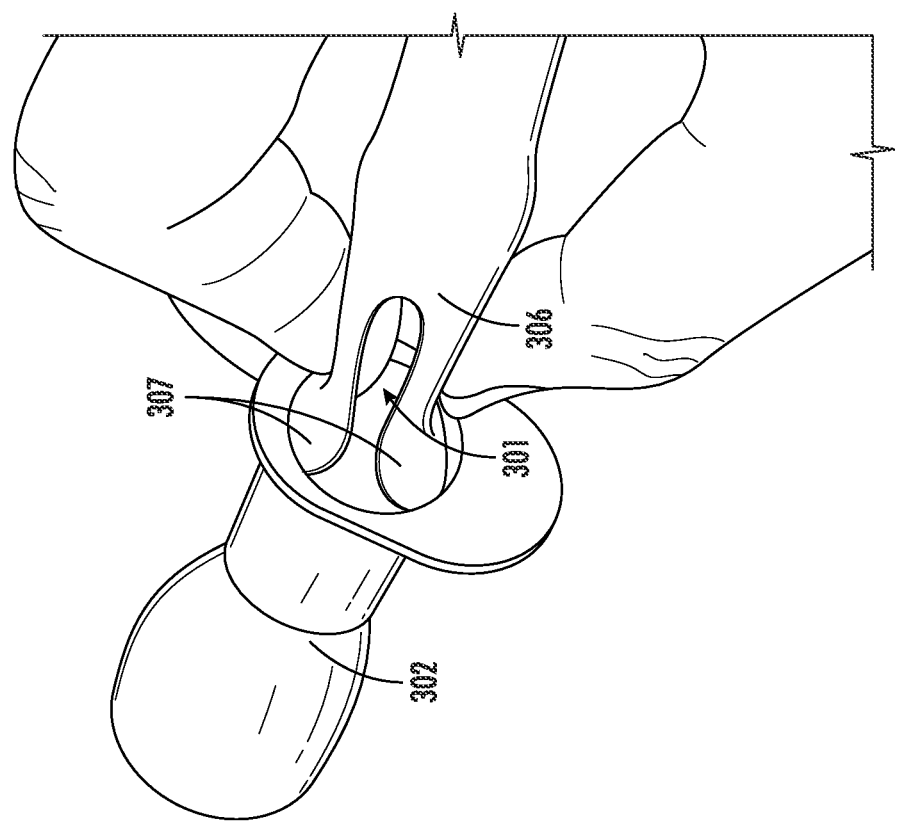
Figure 15A:
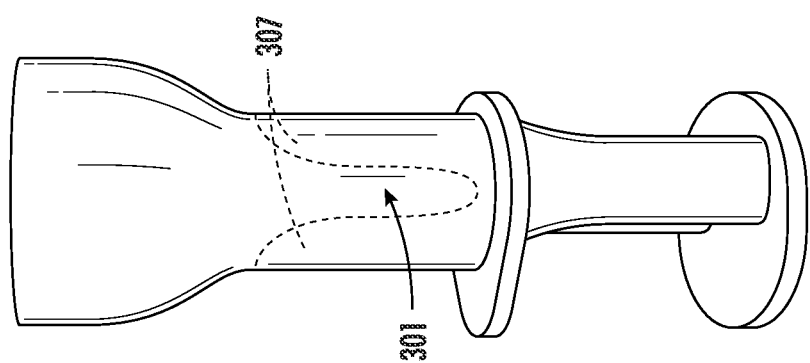
Figure 16A:
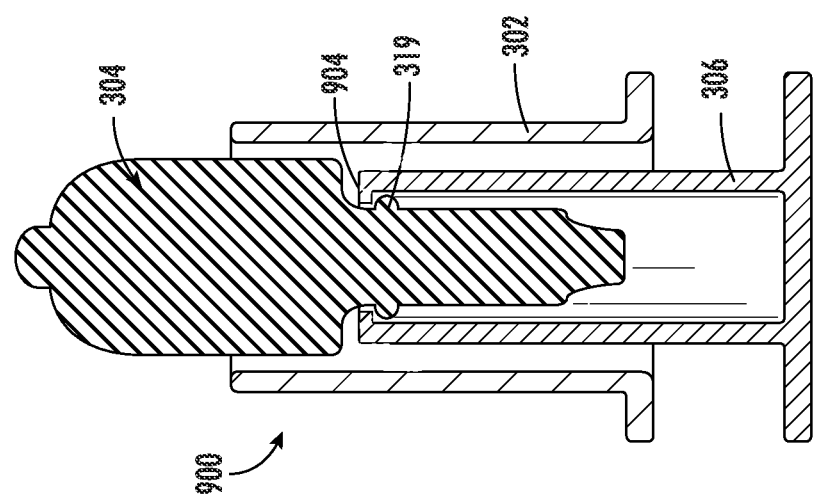
Figure 17B:
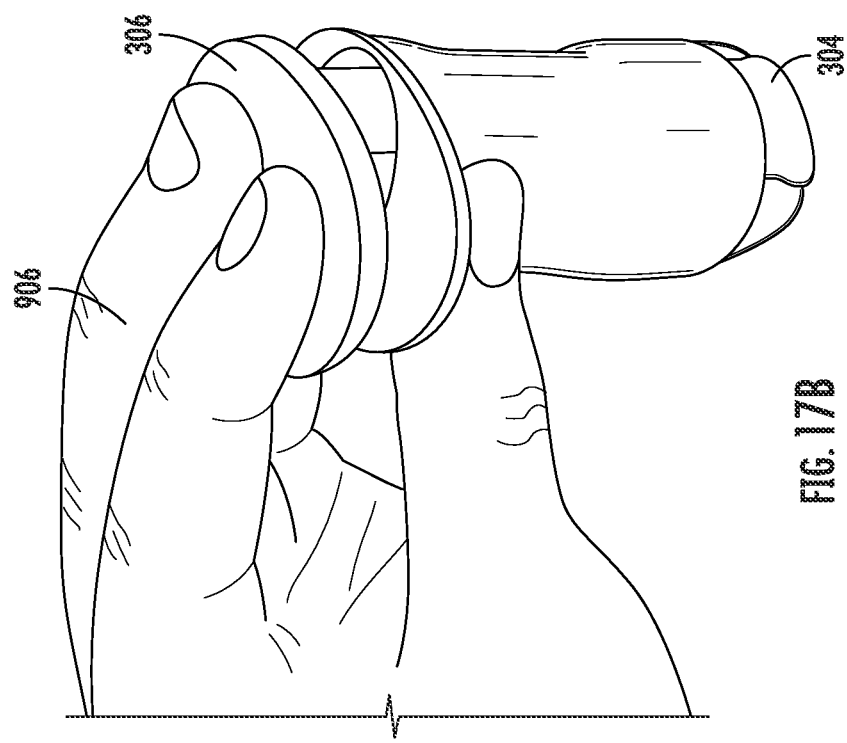
Figure 17A:
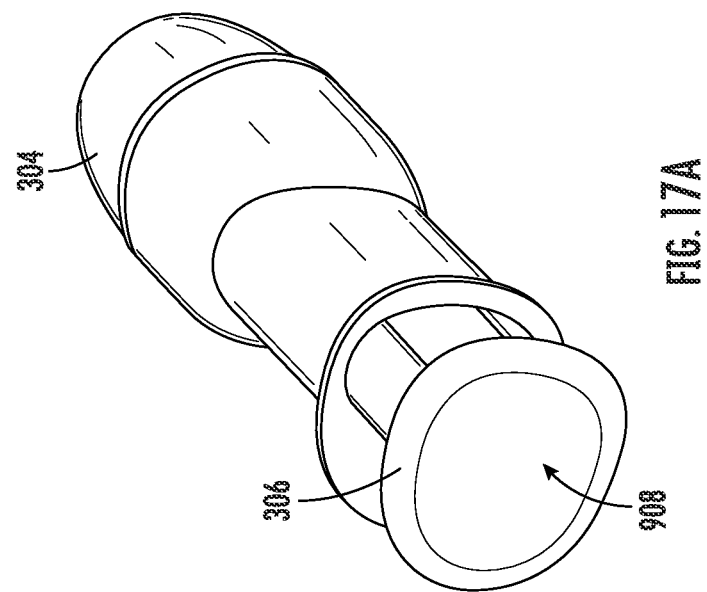
Figure 18:
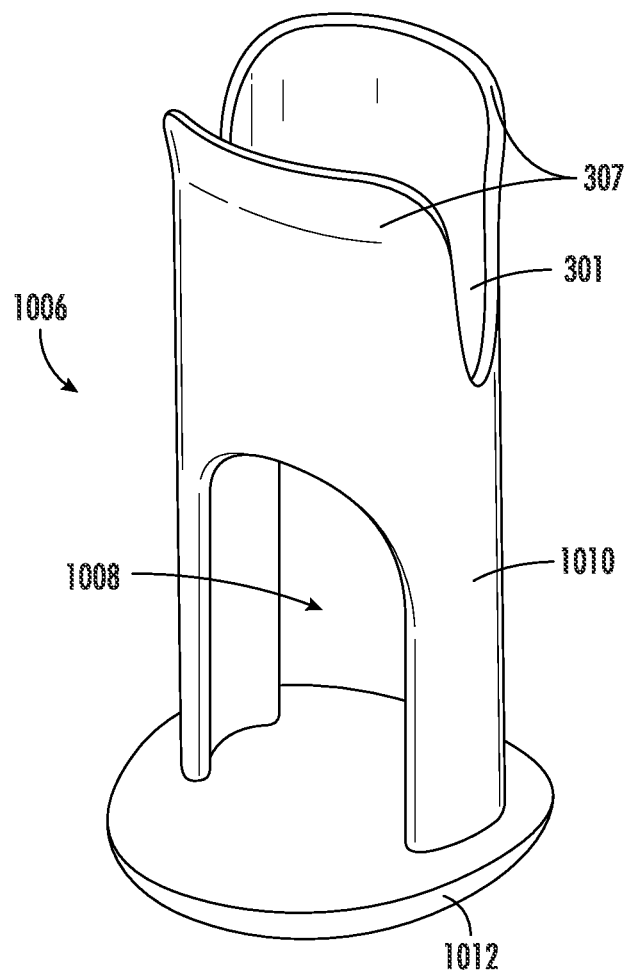
Figure 19:
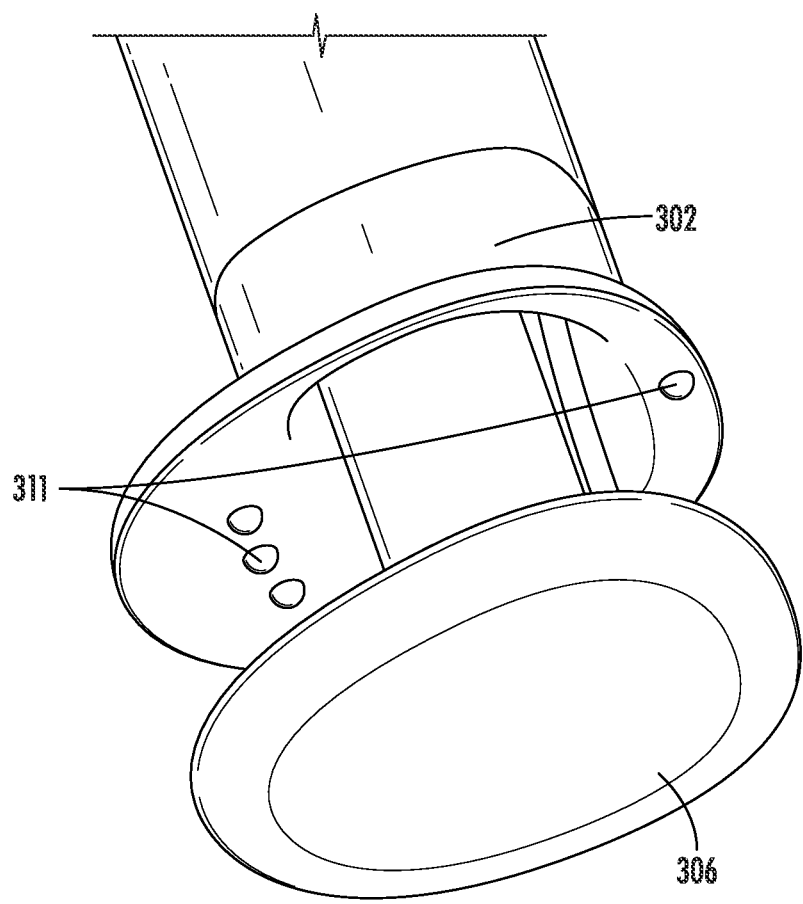

FIGS. 5A-G show another alternative embodiment of the pessary applicator device of the present disclosure;

FIG. 6 shows another alternative embodiment of the pessary applicator device of the present disclosure;

FIG. 7 shows another alternative embodiment of the pessary applicator device of the present disclosure;

FIG. 8 shows another alternative embodiment of the pessary applicator device of the present disclosure;

FIG. 9 shows another alternative embodiment of the pessary applicator device of the present disclosure;

FIG. 10 shows another alternative embodiment of the pessary applicator device of the present disclosure;

FIG. 11 shows another alternative embodiment of the pessary applicator device of the present disclosure;

FIG. 12 shows another alternative embodiment of the pessary applicator device of the present disclosure;

FIG. 13 shows another alternative embodiment of the pessary applicator device of the present disclosure;

FIGS. 14A-F show the manner of loading and operation of the pessary applicator device of the present disclosure;

FIGS. 15A and B show the manner of installing the plunger in the barrel of the pessary applicator device of the present disclosure;

FIGS. 16A and B show other alternative embodiments of the pessary applicator device of the present disclosure;

FIGS. 17A and B show another alternative embodiment of the pessary applicator device of the present disclosure;

FIG. 18 shows another alternative embodiment of the pessary applicator device of the present disclosure; and FIG. 19 shows another alternative embodiment of the pessary applicator device of the present disclosure.

DESCRIPTION OF THE INVENTION

Certain exemplary embodiments will now be described to provide an overall understanding of the principles of the structure, function, manufacture, and use of the device and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure. Further, in the present disclosure, like-numbered components of the embodiments generally have similar features, and thus within a particular embodiment each feature of each like-numbered component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Further, to the extent that directional terms like top, bottom, up, or down are used, they are not intended to limit the systems, devices, and methods disclosed herein. A person skilled in the art will recognize that these terms are merely relative to the system and device being discussed and are not universal.

Figure 1:
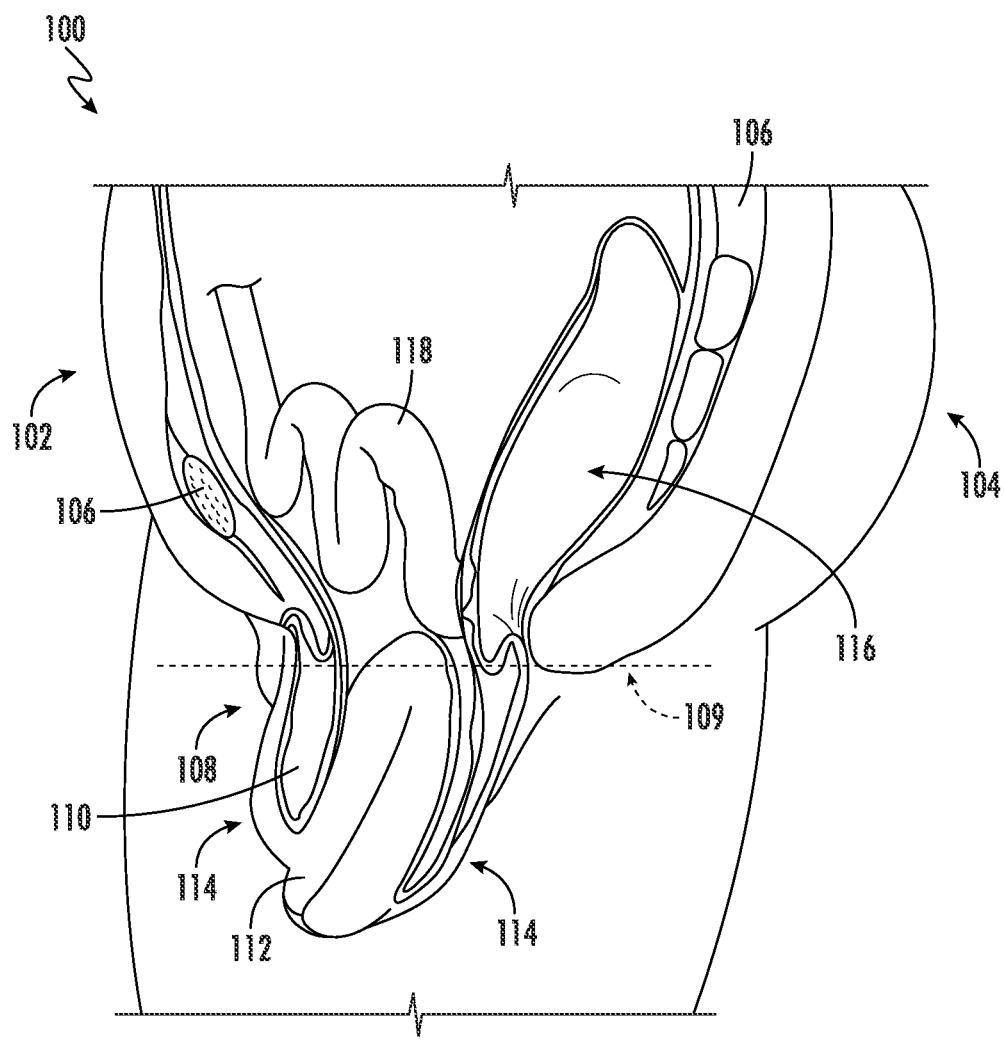
FIG. 1 is a cross sectional view of the pelvic organs in a prolapsed state, according to the prior art.
Figure 2A:
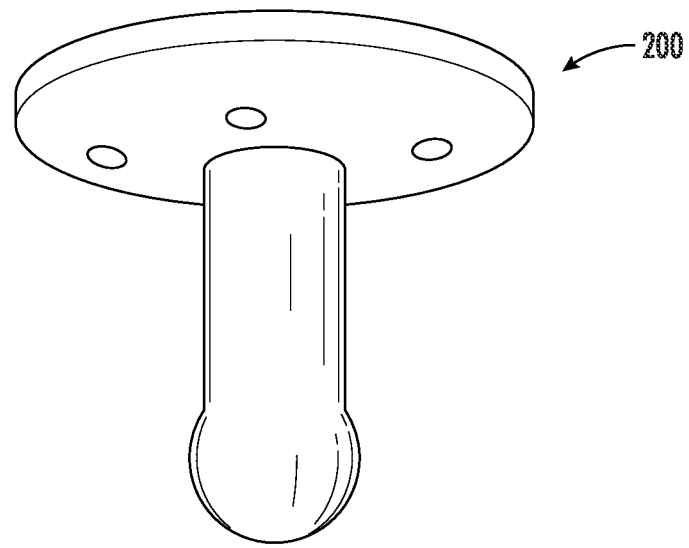
FIGS. 2A-2B show a prior art pessary device.
Figure 2B:
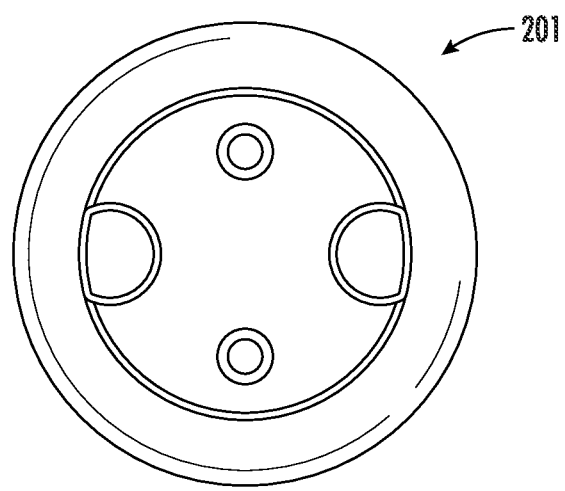
Figure 3:
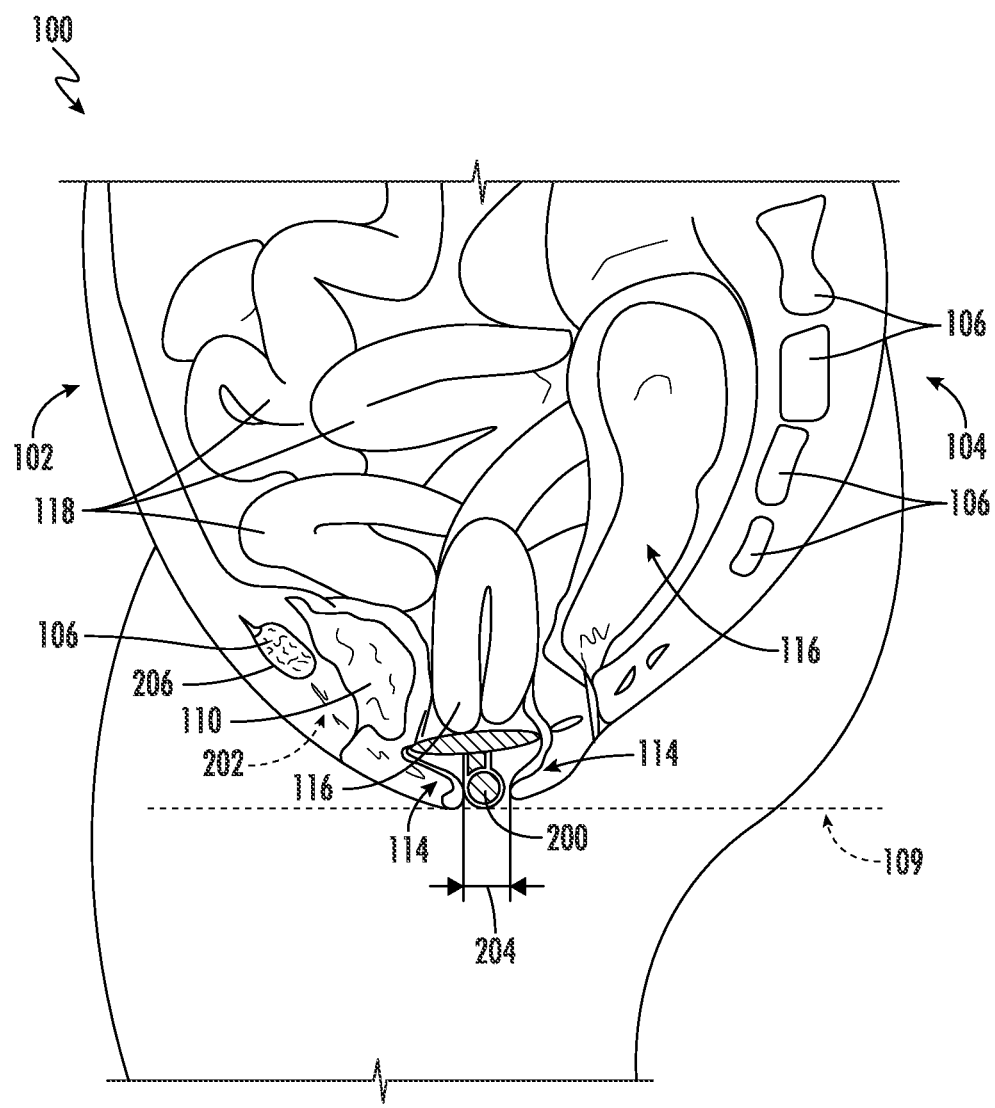
FIG. 3 shows a prior art pessary device inserted in place in a patient.
Figure 4A:
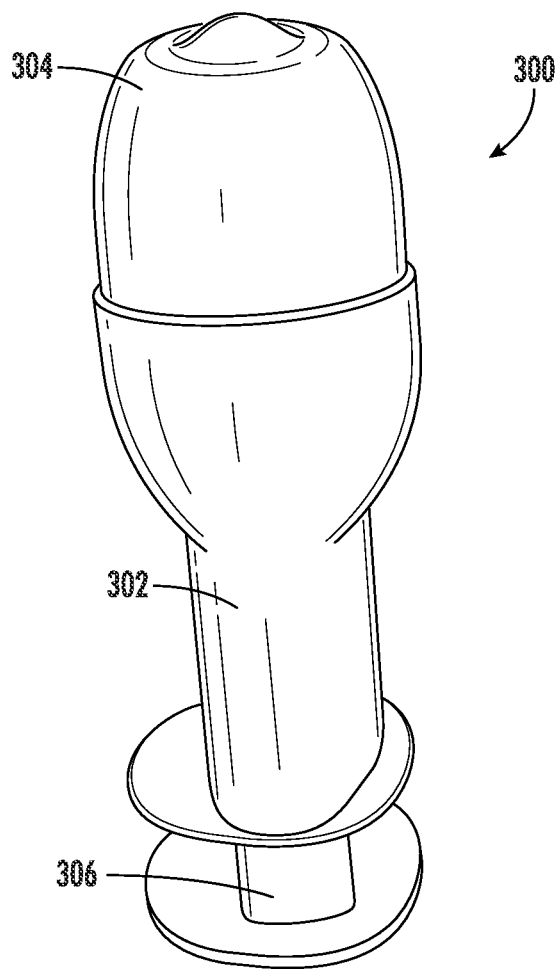
FIGS. 4A and 4B shows a pessary applicator device according to one embodiment of the present disclosure.
Figure 4B:
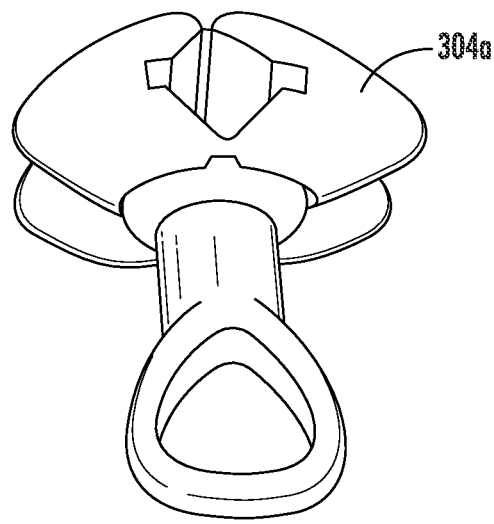

In accordance with the present disclosure, a new and novel pessary applicator device facilitates the insertion of various pessary devices. In general, as shown in FIGS. 4A and 4B, the applicator 300 in accordance with the present disclosure includes a two-part assembly. First, the applicator 300 can include a barrel 302 that is sized to receive, for example, a collapsible pessary 304. In some embodiments, the pessary 304 can be the same, or substantially the same, as the pessary disclosed in co-pending U.S. patent application Ser. No. 16/832,839 entitled PESSARY FOR PELVIC ORGAN PROLAPSE, incorporated by reference in its entirety herein. The aforementioned pessary 304 can be is made of silicone and is substantially domed in shape with an attached stem. During insertion, the pessary 304 can be elongated, bending at the hinges, into a more cylindrical shape. However, the natural state of the pessary, shown at 304a, is its supportive state or flattened state, so it must be forced into and held in its elongated state. The barrel 302 of the applicator 300 is designed to hold the pessary 304 in its collapsed state during insertion and expel it into the vaginal canal once inserted. Alternatively, the barrel 302 itself can be designed to receive any pessary device.

Second, the applicator 300 includes a plunger 306 which is telescopically received within the barrel 302 to eject the pessary 304 from the barrel 302 when in the correctly positioned in the inserted location. The plunger 306 generally includes a body portion as will be described in detail below, that has various shapes that are sized and shaped to be slidably received within the lower portion of the barrel 302. For example, if the lower portion of the plunger 302 has an oval shape, then the portion of the plunger body received within the barrel 302 should have a generally outer oval shape as well. In some embodiments described below the top end of the plunger body may include arms or other structure to receive a portion of a pessary, where the plunger can apply an ejection force.

Most generally, the barrel has a tubular shape with an opening extending from a top end to a bottom end thereof. A plunger having a dispensing end and an activation end opposite the dispensing end is telescopically received within the opening in the barrel. The plunger has a loading position wherein the dispensing end is retracted within the top end of the opening in the barrel and the dispensing end is configured and arranged to at least partially receive a pessary. Application of pressure to the activation end of the plunger induces telescopic movement of the dispensing end of the plunger within the barrel towards the top end and ejects the pessary from the barrel. The various embodiments all share the same general assembly, and each embodiment will be discussed below. One having ordinary skill in the art will understand that each of the embodiments include features which can be combined with other embodiments.

Figure 5A:
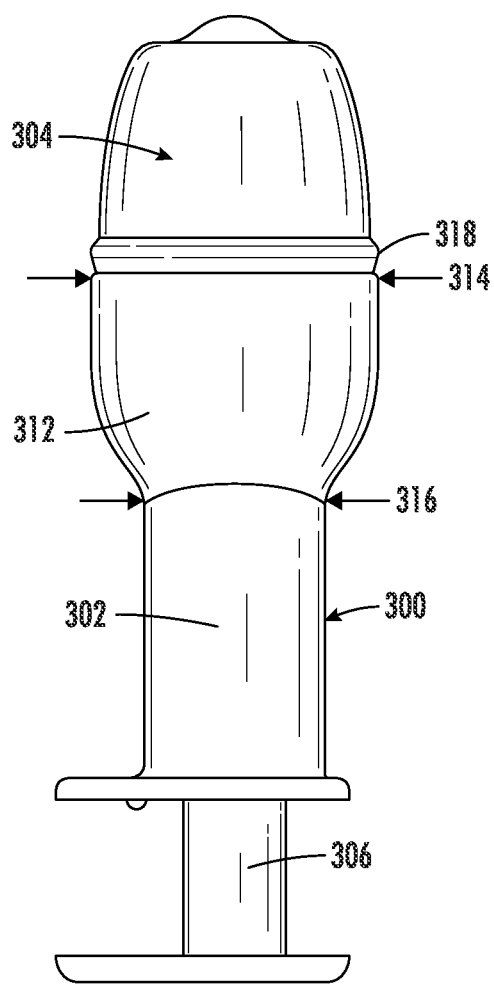
Figure 5B:
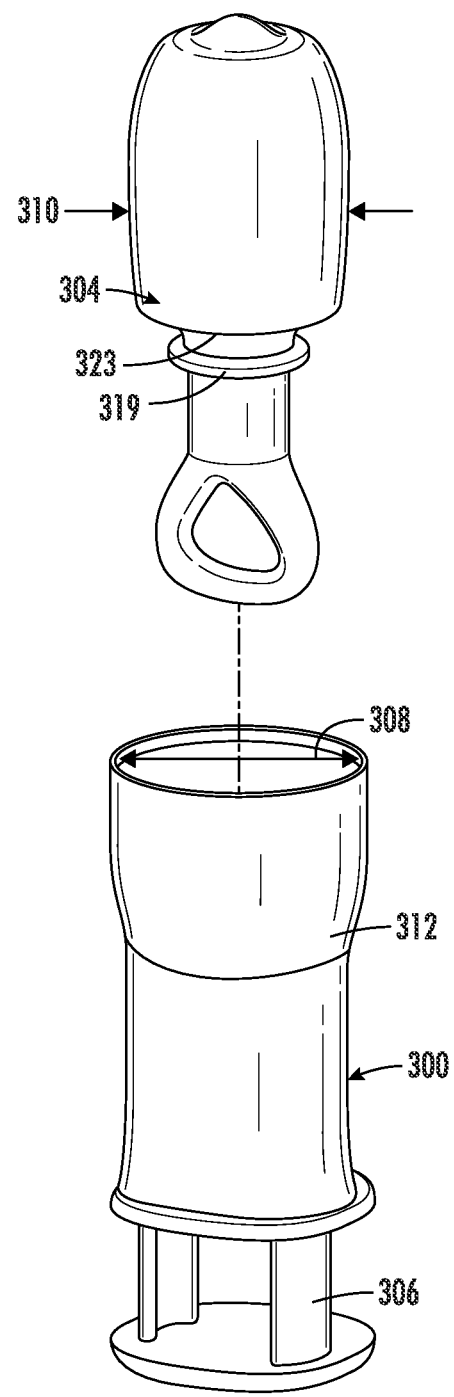

Turning now to FIGS. 5A-D, a preferred embodiment of the pessary applicator device 300 of the present disclosure is illustrated. In the illustrated embodiment, the applicator 300 holds the pessary 304 collapsed by putting pressure on the outside of the pessary 304. The barrel 302 can have a generally circular inner diameter 308 that, at its widest, is the roughly the diameter of the widest part 310 of the pessary 304 in its collapsed state, or the state in which it will be inserted into the vaginal canal. The portion of the barrel that holds the pessary 304 can be generally "chalice" 312 shaped such that the top most edge has a first diameter 314 and narrows down to a second smaller diameter 316. In one embodiment, the top part of the barrel is substantially chaliced in shape, narrowing from the widest diameter. The height of the chalice is such that the bottom arms of the pessary, below the central hinge 318, are covered by the chalice, but the top arms, above the central hinge, are exposed, as shown in FIG. 5A. In the illustrated embodiment of FIG. 5A-G, the diameter 314 and height of the top of the applicator allows the hinge of the pessary 304 to protrude over the edge of the top of the applicator, protecting the user from the edge of the barrel 302 during insertion.

Figure 5C:
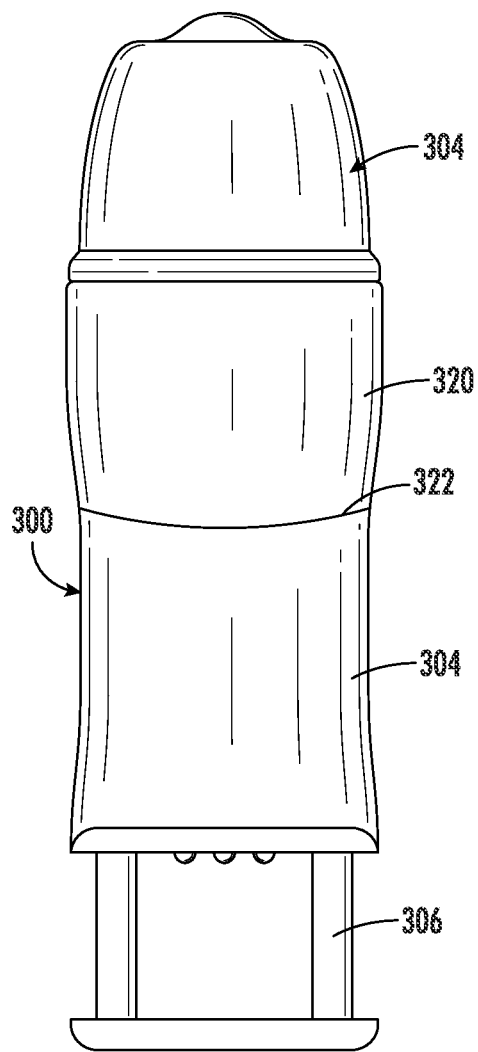
Figure 5D:
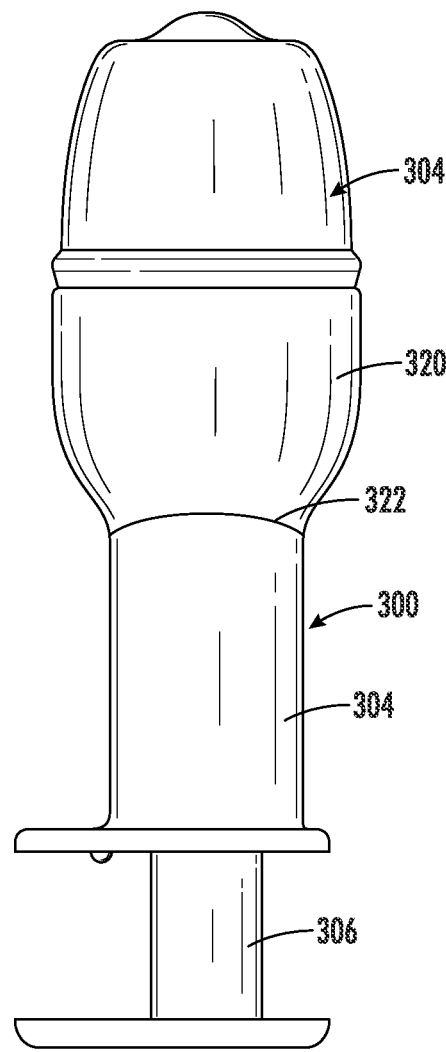
Figure 5E:
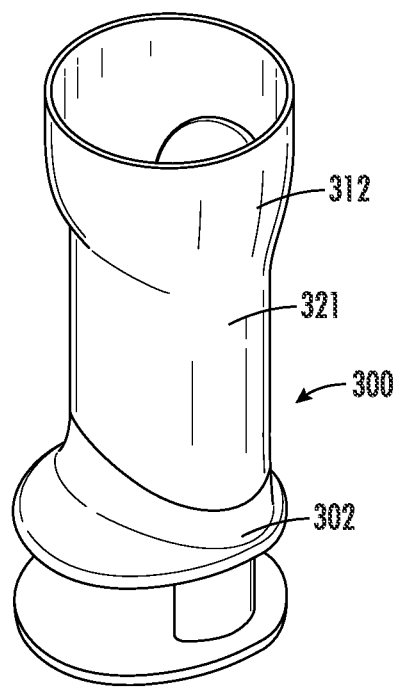
Figure 5F:
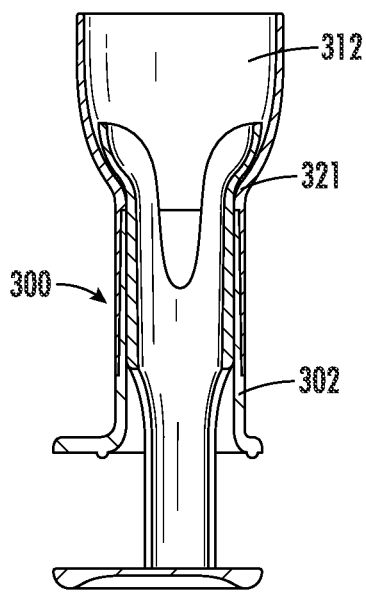
Figure 5G:
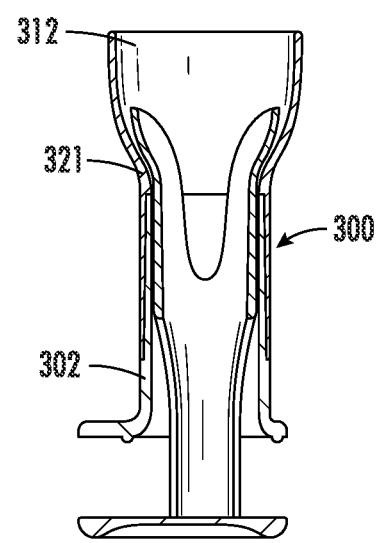

In some embodiments, the top of the applicator 300 may be overmolded 320 with a soft material, such as a flexible polymer or rubber, to protect the user from the edge of the barrel 302 during insertion, as seen in FIGS. 5C and 5D. In one embodiment, the parting line 322 between the overmold 320 and the rest of the barrel 304 may be roughly sinusoidal in shape, creating grips to hold the barrel 302 during pessary 304 loading. As seen in FIGS. 5E and 5F the overmold 321 may form the entire chalice 312 section of the barrel 302. The overmold 321 is a softer material, such as a stiff rubber or other suitable flexible polymer, such that the chalice 312 is formed by the flexible polymer and the bottom portion of the barrel 302 is backed by a rigid polymer. This construction enables the rigid polymer part to be reused in connection with different chalice sizes.

In alternative embodiments, the barrel 402 can be formed from a single material, as shown in the pessary 400 of FIG. 6. In one embodiment, the diameter 514 and height of the top of the applicator 500 cover the central hinge 318 of the pessary 304, as shown in FIG. 7.

The bottom portion of the barrel may take multiple shapes. In one embodiment, as shown in FIG. 8, the lower portion 602 of the barrel can be substantially oval in cross section, creating flatter areas 604 for finger placement. It another embodiment, as shown in FIG. 9, concave cut outs 606 in the lower portion 602 oval cross section create pads for secure finger placement. At the base of the barrel, surfaces perpendicular to the axis of the barrel form grips 608. In the forgoing discussion, only one grip is discussed; however, it is contemplated that the applicators may include two or more grips spaced about the exterior of the applicator.

In one embodiment, shown in FIG. 10, the grips, on both the barrel and the plunger, are small grips 610 (<6 mm) to prevent the user's thumb and finger from slipping off the barrel when ejecting the pessary in a "two-sided" grip where in the applicator is held between the user's thumb and middle or 4$^{th}$ finger on the barrel and the index or middle finger on the plunger. In another embodiment, as shown in FIG. 11, the grips, on both the barrel and the plunger, are larger barrel grips 612 and plunger grips 614 (>6 mm) to allow for a "syringe style" grip, wherein the applicator is held between the users two fingers on the barrel and thumb on the plunger. In another embodiment, as shown in FIG. 12, at least one of the grips, on both the barrel and the plunger, is long enough to allow for a "one-sided" grip, wherein the applicator is held between the user's thumb on the barrel and one or more fingers on the plunger. Alternatively, the size of the grips, on both the barrel and the plunger, can be sized for proper ergonomics for users of different hand sizes.

In some embodiments, as shown in FIG. 13, the entire applicator 700 can have a generally cylindrical cross-sectional shape wherein the barrel 702 and plunger 706 are cylindrical and circular in cross section. Further, the barrel 702 does not include a taper or chalice shaped top but is consistent in cross section along its length.

Figure 14C:
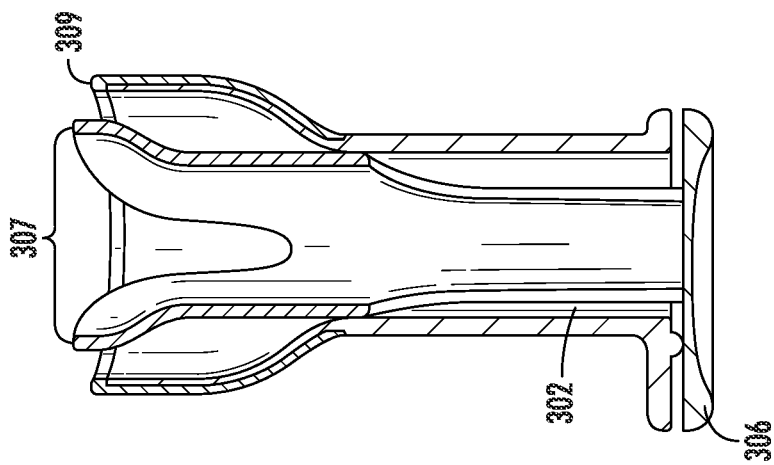
Figure 14B:
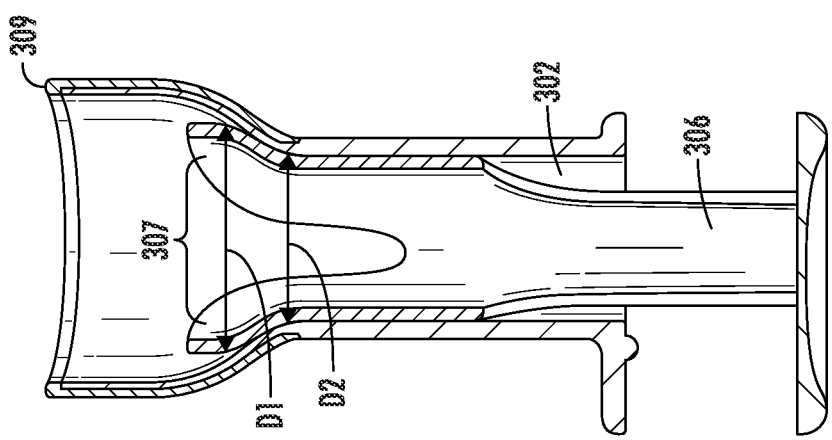
Figure 14A:
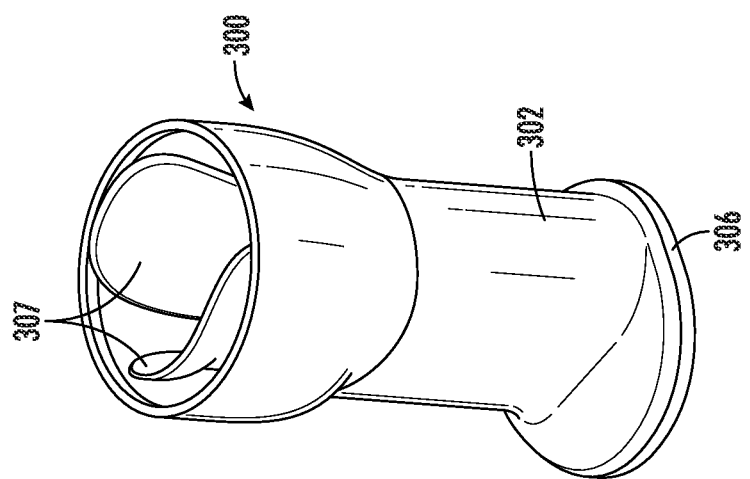
Figure 14F:
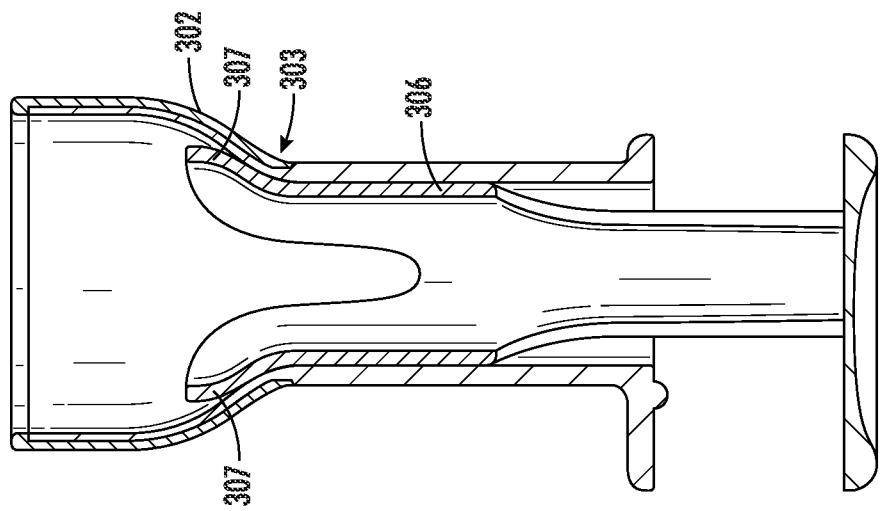
Figure 14E:
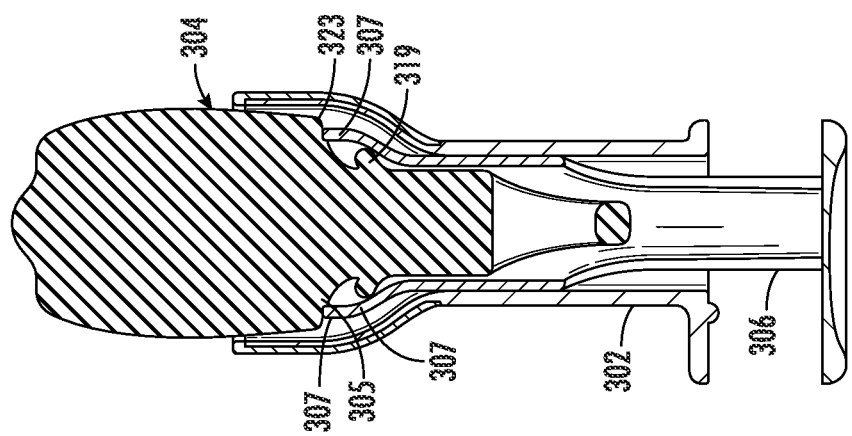
Figure 14D:
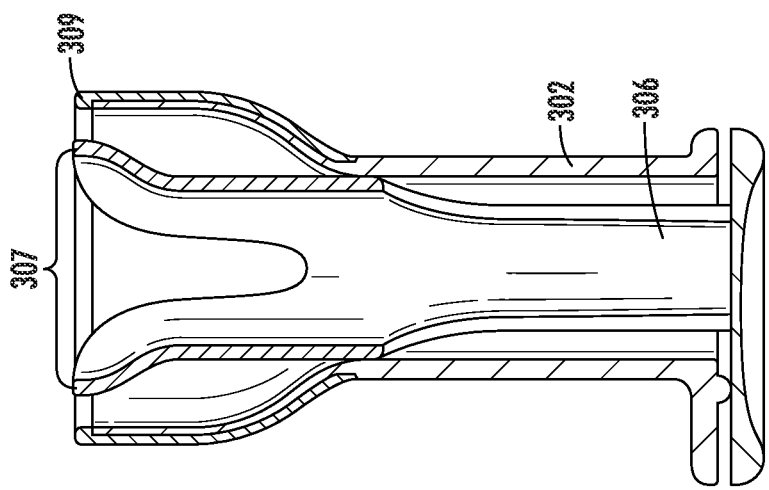

Turning now to FIGS. 14A-F, the pessary is ejected from the pessary applicator 300 with a plunger 306, which telescopically moves inside the barrel 302, along the axis of the barrel. When pressed, the plunger 306 puts pressure on the underside of the pessary 304, expelling the pessary from the top of the barrel. In the "loading state," as seen in FIG. 14B, the top of the plunger 306 includes arms 307 sit below the top edge 309 of the chalice/barrel, such that the pessary can be loaded into the applicator. In the "ejected state," as seen in FIGS. 14C and 14D, the top of the plunger arms 307 are at the top edge 309 of the barrel 302, having pushed the pessary out of the applicator and into the vaginal canal. Further, as shown at FIG. 14B, the plunger 306 has an upper chalice shaped opening such that a first diameter $D_1$ near the topmost edge is larger than a second diameter $D_2$ at an intermediate location lower than the top most edge. Alternatively, as shown in FIG. 14D, the arms 307 of the plunger 306 may be just below, or just above, the topmost edge 309 of the barrel 302.

As shown in FIG. 14E, the top of the plunger arms 307 place a pressure on the underside 305 of the bottom of the pessary 304, namely, between the bottom hinge 323 and a bump feature 319. As the plunger 306 is pressed upward within the barrel 302, the force is transmitted to the pessary 304 to eject the pessary 304 from the barrel 302. The location of contact and force transmission being between the bottom hinge 323 and the bump feature 319 can aid in expelling the pessary in the vaginal canal.

In the chaliced embodiment of the barrel 302, the shape of the plunger 306 may follow the chaliced shape of the barrel 302, as shown in FIG. 14F. The sharp transition 303 from the bottom of the chalice to the vertical section of the grip creates a stop between the barrel and the plunger, indicating to the user that the applicator is in the loading state. If the user pulls the plunger beyond the loading state, the top of the plunger begins to collapse in diameter, making it challenging to load the pessary. This stop prevents the user from pulling the plunger too low for loading.

In an embodiment, illustrated in FIGS. 15A and 15B, a throughcut slot 301 along the plunger 306 that extends parallel to the long axis of the plunger, can define the arms 307 which allows the top of the plunger to flex, such that it may be separated from the barrel 302 by pulling the plunger 306 away from the barrel 302. The slot 301 facilitates cleaning. As the arms 307 of the plunger 306 are able to flex, they can deform to a smaller diameter to fit within the lower portion of the barrel 302. Separating the barrel from the plunger may aid in cleaning the applicator. The plunger 306 may be replaced into the barrel 302 by pinching to flex the top arms 307 of the plunger 306 together, as shown in FIG. 15B, and reinserting it at the barrel base.

In another embodiment 800, as shown in FIG. 16A, the barrel 302 can include an interior stop 802 that can be in the form of a dimple or lip on an inner surface of the barrel. The stop on the barrel may indicate the loading state. In the illustrated embodiment, the plunger 306 can have an upper rim 804, extending radially outward from the plunger, which can interfere with the stop to prevent the plunger from being withdrawn below the stop. Additionally, in this embodiment, the plunger may not include a finger grip to allow the plunger to be pushed all the way through the top of the barrel for removal when cleaning is needed.

Figure 16B:
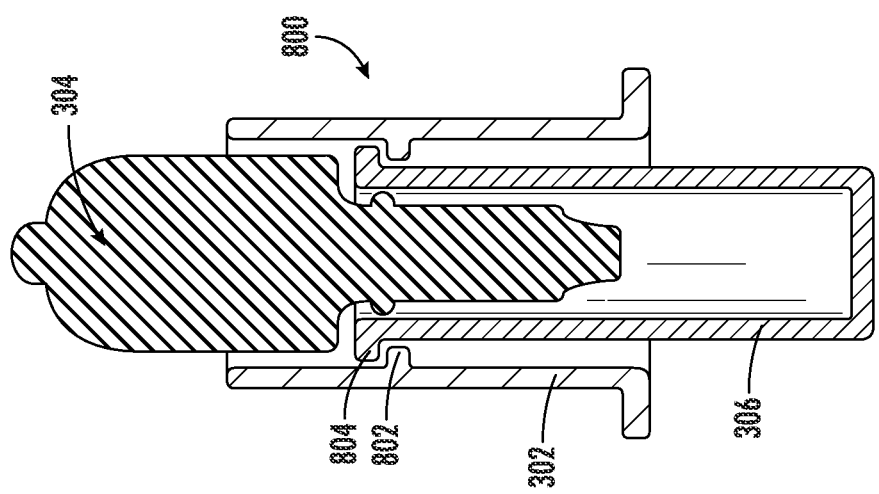

In another embodiment 900, as shown in FIG. 16B, the barrel 302 may have no stop, such that the plunger 306 moves freely into and out of the barrel 302. Thus, the plunger 306 may be inserted into the barrel 302 at any time, including after the barrel 302 with the loaded pessary 304 have been inserted into the vaginal canal. The plunger 306 in the illustrated embodiment, may include a radially inner lip 904 which can engage the underside of the pessary 304 to eject it from the barrel 302.

In some embodiments, as illustrated in FIGS. 17A and 17B, the bottom of the plunger 306, where the user 906 pushes on the plunger to expel the pessary, may be concave in shape 908, giving the users 906 a stable touchpoint to exert pressure onto. The concave shape 908 of the bottom of the plunger 306 can be sized to stably receive one or more fingers of the user 906.

As shown in FIG. 18, the vertical section of an alternate plunger 1006 may include a through-cut 1008 to enable access to the inner surfaces of the plunger 1006 for cleaning. In the illustrated embodiment, the through-cut 1008 is positioned through the body 1010 of the plunger above the base 1012 has a generally arch shape, but any shaped opening can be used that retains the structural integrity of the plunger to transmit axial forces from the bottom of the plunger to a pessary being ejected, as discussed above.

To prevent the pinching of any tissue or hair between the grip of the plunger 306 and the grip of the barrel 302 in the "ejected state," the applicator can include a feature to prevent the bottom surface of the barrel from being flush in contact with the topside of the push surface of the plunger. This feature can create a gap which can cause a separation that may be caused by concavity on either surface or both surfaces or raised textures, such as small bump-like features 311, on either surface, as shown in FIG. 19.

It would be appreciated by those skilled in the art that various changes and modifications can be made to the illustrated embodiments without departing from the spirit of the present disclosure. All such modifications and changes are intended to be covered by the appended claims.

The invention claimed is:

1. An applicator for a pessary device, comprising:
   a tubular barrel having a top portion having a top open end and a bottom portion having a bottom open end; the top portion being chalice-shaped with the top open end being larger than the bottom open end;
   a plunger having a dispensing end with arms extending upwardly and laterally outward from the plunger and an activation end opposite the dispensing end telescopically received in the the tubular barrel, the dispensing end with upwardly extending arms being larger than the bottom open end; the dispensing end being telescopingly actuatable within the chalice-shaped top portion of the opening tubular barrel between a lower loading position and an upper dispensing position; the dispensing end being configured and arranged to at least partially receive a pessary, and an upper dispensing position;

wherein pressure applied to the activation end of the plunger induces telescopic movement of the dispensing end of the plunger within the barrel towards the top open end and ejects the pessary from the barrel; the arms of the dispensing end residing within the chalice-shaped top portion of the tubular barrel during telescopic actuation between the lower loading position and the upper dispensing position.

2. The applicator of claim 1, the tubular barrel further comprising:
a transition line extending around the barrel between the top and bottom ends.

3. The applicator of claim 2, wherein the barrel has an upper chalice-shaped opening having a first diameter above the transition line and a second diameter below the transition line, wherein the first diameter is larger than the second diameter.

4. The applicator of claim 3, wherein an outer surface and the top end of the barrel above the transition line includes an overmolded coating of flexible polymer.

5. The applicator of claim 3, wherein an upper portion of the barrel above the transition line is formed from an overmolded flexible polymer.

6. The applicator of claim 2, wherein the transition line is sinusoidal as it extends about the barrel.

7. The applicator of claim 2, wherein an outer surface and the top end of the barrel above the transition line includes an overmolded coating of flexible polymer.

8. The applicator of claim 2, wherein an upper portion of the barrel above the transition line is formed from an overmolded flexible polymer.

9. The applicator of claim 1, wherein the barrel has a lip extending outwardly around at least a portion of the bottom end forming a barrel finger grip.

10. The applicator of claim 9, wherein the barrel finger grip includes a raised texture on a bottom surface thereof facing a bottom end of the plunger to create a gap therebetween to prevent contact between the barrel finger grip and the bottom end of the plunger.

11. The applicator of claim 1, the plunger further comprising:
a lip extending outwardly around at least a portion of the bottom end forming a plunger finger grip.

12. The applicator of claim 11, wherein a barrel finger grip includes a raised texture on a bottom surface thereof facing the lip of the plunger to create a gap therebetween to prevent contact between the barrel finger grip and the lip of the plunger.

13. The applicator of claim 1, wherein the upwardly extending arms flare outwardly to match the chalice-shaped top portion of the barrel.

14. The applicator of claim 13, wherein the upwardly extending arms are flexible and deflectable inwardly to enable insertion of the plunger into the bottom open end of the barrel and through the barrel and into the chalice-shaped top portion; whereby the upwardly extending arms expand outwardly upon entry into the chalice-shaped top portion.

15. The applicator of claim 1, wherein the tubular barrel is formed from a rigid polymer.

16. The applicator of claim 1, wherein the dispensing end engages a bottom surface of a pessary device inserted therein allowing pressure applied to a bottom end of the plunger to be transferred to the pessary device, ejecting the pessary device upwardly from the barrel.

17. The applicator of claim 1, wherein the barrel has a lip extending outwardly around at least a portion of the bottom end forming a barrel finger grip and a lip extending outwardly around at least a portion of the bottom end forming a plunger finger grip; at least one of the lip of the barrel finger grip and lip of the plunger finger grip includes a raised texture thereon to create a gap therebetween to prevent contact between the barrel finger grip and the plunger finger grip.

18. The applicator of claim 1, wherein the plunger defines a slot therein that extends parallel to the long axis of the plunger.

19. The applicator of claim 1, wherein the plunger defines a through-cut opening that extends transversely through the plunger.

* * * * *